United States Patent [19]

Cervoni et al.

[11] 4,086,363
[45] Apr. 25, 1978

[54] TREATMENT OF ASTHMA

[75] Inventors: Peter P. Cervoni, New Rochelle; Peter S. Wolf, Port Chester, both of N.Y.

[73] Assignee: USV Pharmaceutical Corporation, Tuckahoe, N.Y.

[21] Appl. No.: 778,042

[22] Filed: Mar. 16, 1977

[51] Int. Cl.² ............................................ A61K 31/135
[52] U.S. Cl. ........................................................ 424/330
[58] Field of Search .......................................... 424/330

[56] References Cited

PUBLICATIONS

Chemical Abstracts 81:114565r (1974).
Goodman & Gilman, "The Pharmacological Basis of Therapeutics" (Textbook), 1966, pp. 484–510.

Primary Examiner—Leonard Schenkman
Attorney, Agent, or Firm—Leon E. Tenenbaum

[57] ABSTRACT

The symptoms of asthma are relieved by the administration of p-hydroxy-N-(1-methyl-3-phenylpropyl)-norephedrine.

2 Claims, No Drawings

TREATMENT OF ASTHMA

This invention relates to the treatment of asthma and the prevention of asthmatic symptoms. It particularly relates to the use of the compound, p-hydroxy-N-(1-methyl-3-phenylpropyl)norephedrine (hereinafter referred to as "nylidrin") in such prevention and treatment.

Beta-adrenergic stimulators have been shown to be useful in the treatment of asthma and the relief of its symptoms by either oral administration or inhalation. Examples of such stimulators are epinephrine, ephedrine, isoproterenol, metaproterenol, terbutaline and salbutamol. It is believed that the beta-adrenergic stimulators achieve this effect by stimulation of the $beta_2$-receptors in the smooth muscle of the trachea.

Although the aforementioned compounds are effective in the reduction or prevention of asthmatic symptoms, they have certain drawbacks which limit their use.

Some of the compounds (isoproterenol and epinephrine) have a rather short duration of activity requiring repeated dosages. Some (isoproterenol and metaproterenol) produce undesirable cardiovascular effects such as tachycardia and hypotension. Salbutamol produces tremors while terbutaline, isoproterenol and ephedrine produce tachyphylaxis.

It is, accordingly, an object of the present invention to treat asthma and reduce or eliminate its symptoms by the administration of a bronchodilator which has less cardiovascular side effects than bronchodilators now in use.

It is another object of the present invention to provide a method for the treatment of asthma and the reduction or elimination of its symptoms, which is rapid-acting and of relatively long duration.

We have now found that nylidrin, a compound described in U.S. Pat. Nos. 2,661,372 and 2,661,373, has a rapid effect in reducing and eliminating the symptoms of asthma which effect is of long duration without producing any undesirable cardiovascular side effects.

Nylidrin has been regarded as a beta-adrenergic stimulant but it does not affect the $beta_2$-receptors in the smooth muscle of the trachea. Nevertheless, despite this property, nylidrin surprisingly is able to counteract the effect of histamine and other bronchoconstrictors on the smooth muscle of the trachea.

Nylidrin was evaluated for its activity by comparing it to isoproterenol for bronchodilator effects in anesthetized ventilated dogs. Both nylidrin and isoproterenol inhibited histamine-induced increases in airway resistance, indicating bronchodilator activity. Following intraveneous administration, isoproterenol was highly active, but for a brief duration. By contrast, nylidrin was effective over a far longer period. Nylidrin was also effective when given into the duodenum, a model for oral administration.

The method used in carrying out these tests is described in J. Pharmacol. Exper. Therap. 189, 445 (1947). It is recognized that the bronchodilator activity of a compound in inhibiting histamine is an excellent indication of its activity in relieving asthmatic attacks in humans (J. Pharm. Pharmacol. 28, 369 (1976)).

Nylidrin was prepared according to the methods described in U.S. Pat. Nos. 2,661,372 and 2,661,373 and may be used as the free base or as a pharmaceutically acceptable, non-toxic acid addition salts such as, for example, the hydrochloride, phosphate, sulfate, lactate, acetate, benzoate, citrate, and the like. The compound may be administered orally in the form of tablets, capsules, lozenges, syrups and the like or by inhalation, in effective daily dosages ranging from about 10 to 50 mg. per day. Obviously, the physician will ultimately determine the dosage which will be most suitable for a particular individual, and will vary with age, weight and response of such individual.

Examples 1–8 describe the preparation of various pharmaceutical dosage forms for administration.

EXAMPLE 1

| Ingredients | Quantity per Tablet |
|---|---|
| 1. Nylidrin HCl, NF | 60 g. |
| 2. Lactose, USP | 600 g. |
| 3. Microcrystalline Cellulose, NF | 134 g. |
| 4. Directly compressible Starch | 200 g. |
| 5. Magnesium Stearate, USP | 6 g. |
| | 1000 g. |

Method of Preparation
- A. Blend 1, 2, 3, and 4. Pass through a #30 mesh screen.
- B. Add 5 and blend.
- C. Compress into 9/32 inch tablets using a suitable tablet press to obtain about 10,000 mg. tablets.

EXAMPLE 2

| Ingredients | Quantity per Tablet |
|---|---|
| 1. Nylidrin HCl, NF | 120 g. |
| 2. Lactose, USP | 870 g. |
| 3. Microcrystalline Cellulose, NF | 200 g. |
| 4. Directly compressible Starch | 300 g. |
| 5. Magnesium Stearate, USP | 10 g. |
| | 1500 g. |

Method of Preparation
- A. Blend 1, 2, 3, and 4. Pass through a #30 mesh screen.
- B. Add 5 and blend.
- C. Compress into 5/16 inch tablets using a suitable tablet press to obtain about 10,000 12 mg. tablets.

EXAMPLE 3

| Ingredients | Quantity per Capsule |
|---|---|
| 1. Nylidrin HCl | 6 g. |
| 2. Lactose, USP | 193 g. |
| 3. Magnesium Stearate, USP | 1 g. |
| | 200 g. |

Method of Preparation
- A. Suitable blend 1 with a small portion of 2. Pass through a #40 mesh screen.
- B. Blend Step A mixture wih the remainder of 2.
- C. Add 3 and blend.
- D. Encapsulate the blend in 1000 #4 two-piece hard gelatin capsules which contain 6 mg. each.

EXAMPLE 4

| Ingredients | Quantity per Capsule |
|---|---|
| 1. Nylidrin HCl | 12.0 g. |
| 2. Lactose, USP | 286.5 g. |
| 3. Magnesium Stearate, USP | 1.5 g. |

-continued

| Ingredients | Quantity per Capsule |
|---|---|
| | 300.0 g. |

Method of Preparation
A. Suitable blend 1 with a small portion of 2. Pass through a #40 mesh screen.
B. Blend step A mixture with the remainder of 2.
C. Add 3 and blend.
D. Encapsulate the blend in 1000 #3 two-piece hard gelatin capsules which contain 12 mg. each.

EXAMPLE 5

| Ingredients | Quantity per 1000 ml. |
|---|---|
| 1. Nylidrin HCl | 1.2 g. |
| 2. Sodium Benzoate, USP | 1.0 g. |
| 3. Saccharin Sodium, NF | 0.5 g. |
| 4. Glycerin | 50.0 ml. |
| 5. Sorbitol Solution 70%, USP | 100.0 ml. |
| 6. Sugar, granulated | 500.0 g. |
| 7. FD&C Yellow No. 6 | 0.1 g. |
| 8. Imitation Orange Flavor | 5.0 ml. |
| 9. Water, Purified, USP qs to | 1000.0 ml. |

This composition contains 6.0 mg. of Nylidrin HCl per 5 ml. of syrup.

Method of Preparation
A. Dissolve 1 in about 300 ml. of 9 with agitation.
B. Continue agitation and dissolve 2, 3, and 6 in the batch.
C. Add 4 and 5 and mix until the batch is homogeneous.
D. In a separate container, dissolve 7 in about 10 ml. of 9, and add this solution into the batch mix.
E. Add 8 and bring the batch to volume with 9.
F. Mix until the batch is homogeneous.
G. Filter through a suitable filter press.

EXAMPLE 6

| Ingredients | Quantity per 1000 ml. |
|---|---|
| 1. Nylidrin HCl, NF | 2.4 g. |
| 2. Sorbitol Solution 70%, USP | 80.0 g. |
| 3. Glycerin, USP | 20.0 g. |
| 4. Methylparaben, USP | 1.5 g. |
| 5. Propylparaben, USP | 0.5 g |
| 6. Sodium Citrate (dihydrate), USP | 5.0 g |
| 7. Sugar, granulated | 150.0 g. |
| 8. FD&C Red No,. 4 | 0.1 g. |
| 9. Imitation Cherry Flavor | 4.0 mg. |
| 10. Water, Purified, USP qs to | 1000.0 ml. |

This composition contains 12.0 mg. of Nylidrin HCl per 5 ml. of syrup.

Method of Preparation
A. Dissolve 1 in about 500 ml. of 10 with agitation.
B. Continue agitation and dissolve 6 and 7.
C. Add 2 and 3 and mix until the batch is homogeneous.
D. In a separate container, dissolve 4 and 5 in about 100 ml. of hot (80°) 10. Add to the batch.
E. Prepare separately a solution of 8 in about 10 ml. of 10 and add to the batch. Mix.
F. Add 9 to the batch and bring to volume with 10. Mix until homogeneous.
G. Filter through a suitable filter press.

EXAMPLE 7

| Ingredients | Weight, Per Cent |
|---|---|
| 1. Nylidrin HCl, NF | 2.0 |
| 2. Alcohol, USP | 34.0 |
| 3. Propellant 12 | 64.0 |
| | 100.0 |

Method of Preparation
A. Dissolve 1 in 2 and cool to about 0°.
B. Add chilled 3 in Step A solution.
C. Fill the appropriate quantity in a metered aerosol container.

EXAMPLE 8

| Ingredients | Weight, Per Cent |
|---|---|
| 1. Nylidrin HCl, NF | 1.0 |
| 2. Alcohol, USP | 19.0 |
| 3. Propellant 12 | 30.0 |
| 4. Propellant 114 | 50.0 |
| | 100.0 |

Method of Preparation
A. Dissolve 1 in 2.
B. Fill the appropriate quantity of Step A solution along with a mixture of 3 and 4 in a metered aerosol container.

We claim:
1. A method of treating asthmatic symptoms in a human in need of said treatment which comprises administering to said human an effective amount of p-hydroxy-N-(1-methyl-3-phenylpropyl)-nor-ephedrine or a pharmaceutically acceptable, non-toxic acid addition salt thereof.
2. A method according to claim 1 wherein the salt is the hydrochloride.

* * * * *

UNITED STATES PATENT OFFICE
CERTIFICATE OF CORRECTION

Patent No. 4,086,363  Dated April 25, 1978

Inventor(s) Peter P. Cervoni et al.

It is certified that error appears in the above-identified patent and that said Letters Patent are hereby corrected as shown below:

Column 2, Examples 1 and 2

In heading after "per" change "Tablet" to - - - 10,000 Tablets - - -

Column 2, line 28, After "10,000" and before "mg." insert - - - 6 - - -

Column 2, Examples 3 and 4

In heading after "per" change "Capsule" to - - - 1,000 Capsules - - -

Signed and Sealed this

Thirtieth Day of January 1979

[SEAL]

Attest:

RUTH C. MASON
Attesting Officer

DONALD W. BANNER
Commissioner of Patents and Trademarks